(12) United States Patent
Heim

(10) Patent No.: US 7,025,881 B2
(45) Date of Patent: Apr. 11, 2006

(54) FILTER ARRANGEMENT FOR THE SEPARATION OF BLOOD INTO PLASMA AND CELLULAR COMPONENTS AND DEVICE FOR APPLICATION THEREOF ON THE DONOR

(75) Inventor: Gerd H. Heim, Gladbeck (DE)

(73) Assignee: Heim Medizintechnik GmbH, Gladbeck (DE)

( * ) Notice: Subject to any disclaimer, the term of this patent is extended or adjusted under 35 U.S.C. 154(b) by 0 days.

(21) Appl. No.: 10/110,578

(22) PCT Filed: May 23, 2001

(86) PCT No.: PCT/DE01/01936

§ 371 (c)(1),
(2), (4) Date: Apr. 11, 2002

(87) PCT Pub. No.: WO02/13888

PCT Pub. Date: Feb. 21, 2002

(65) Prior Publication Data

US 2002/0183678 A1 Dec. 5, 2002

(30) Foreign Application Priority Data

Aug. 15, 2000 (DE) .......................... 200 14 311 U (51) Int. Cl.
*B01D 63/00* (2006.01)
(52) U.S. Cl. ............................. 210/257.2; 210/257.1; 210/645; 210/650; 210/321.79; 210/321.8; 210/321.87; 210/651; 210/500.23; 210/188; 604/251; 604/6.04
(58) Field of Classification Search .............. 210/645, 210/650, 651, 321.79, 321.8, 321.87, 321.88, 210/321.89, 321.6, 500.23, 500.24, 3, 257.1, 210/257.2
See application file for complete search history.

(56) References Cited

U.S. PATENT DOCUMENTS 4,025,436 A * 5/1977 Tsuda et al. .............. 210/321.8

(Continued)

FOREIGN PATENT DOCUMENTS

DE 295 16 471 3/1996

(Continued)

OTHER PUBLICATIONS

English Translation of DE 197 33 407 A.*

*Primary Examiner*—W. L. Walker
*Assistant Examiner*—Krishnan S. Menon
(74) *Attorney, Agent, or Firm*—Collard & Roe, P.C.

(57) ABSTRACT

The invention relates to a filter arrangement for the separation of blood into plasma and cellular components, comprising at least one filter element with an inlet line and an outlet chamber in a closed housing, separated by a fine pore membrane. The inlet chamber is connected to an inlet line for donor blood an dan outlet line for cellular components and the outlet chamber is connected to an outlet line for plasma. The arrangement further comprises a device for the production of a backpressure in the filter element, whereby the fine pore membrane is in the form of a U-shaped bundle of n=650 hollow fibers of the type Micro PES-TF 10 from Akzo Faser AG, the ends of which are fixed in an air-tight and germ-tight manner to an aperture plate which seals the open end region of the housing, which is open at just one end, in an air-tight and germ-tight manner. The free length of said fibers between the input and output region, within the housing, is l=27 cm, whereby the inner volume of all the hollow fibers forms the inlet chamber and the outer volume within the housing forms the outlet chamber. The above filter arrangement may thus be integrated in a device for application on the donor, which collects the separated fractions of the donor blood in specially arranged receptacles.

23 Claims, 3 Drawing Sheets

U.S. PATENT DOCUMENTS

| | | | | |
|---|---|---|---|---|
| 4,031,012 A | * | 6/1977 | Gics | 210/321.81 |
| 4,601,712 A | * | 7/1986 | Cole et al. | 604/251 |
| 5,587,070 A | * | 12/1996 | Pall et al. | 210/202 |
| 5,858,238 A | * | 1/1999 | McRea et al. | 210/645 |

FOREIGN PATENT DOCUMENTS

| | | |
|---|---|---|
| DE | 197 33 407 | 2/1999 |
| EP | 0 414 515 | 2/1991 |
| WO | WO 97 32653 | 9/1997 |

* cited by examiner

FILTER ARRANGEMENT FOR THE SEPARATION OF BLOOD INTO PLASMA AND CELLULAR COMPONENTS AND DEVICE FOR APPLICATION THEREOF ON THE DONOR

CROSS REFERENCE TO RELATED APPLICATIONS

Applicant claims priority under 35 U.S.C. §119 of German Application No. 200 14 311.5 filed Aug. 15, 2000. Applicant also claims priority under 35 U.S.C. §120 of PCT/DE01/01936 filed May 23, 2001. The international application under PCT article 21(2) was not published in English.

The invention relates to a filter arrangement for the separation of blood into plasma and cellular components according to the features specified in the introductory part of patent claims 1. Furthermore, it relates to a device for the application of such a filter on the donor according to the features specified in the introductory part of patent claim 12.

Such filter arrangements have been the object of intensive research and development efforts since many years, with the aim of replacing the tested separation method for separating blood by means of a centrifuge, which requires a great amount of expenditure and, furthermore, due to the required refilling measures, is always connected with the risk that the blood may get contaminated by air and therefore with germs as well, with a simple filtration method for producing blood reserves of own or foreign blood, by which the blood can be separated in a sterilized, closed system into both of its individual components, in particular into erythrocytes and plasma, and, furthermore, can be directly preserved separated by components as well. As examples of such efforts, mentioned are here only the objects of DE 197 33 407 A1 and of the publication "Hämatologie" [Hematology] Vol. 1, "Aktueller Stand der Eigenbluttransfusion" [Actual State of the Own Blood Transfusion], Sympomed Publishing Company, Munich 1992, pages 108 to 113, and the published patent document WO 00/62840, which issued from the international patent application PCT/DE 00/01258.

All of these efforts, however, have failed to produce any satisfactory long-term results in the long with respect to clear separation of plasma and cellular components of the respective blood to the greatest possible degree, i.e. following the primary filtration. The hematocrit value in the fraction of the cellular components is in any case in the order of magnitude of 50%, which in no case corresponds with the results that can be obtained with a centrifuge.

The filter systems of the type described above are usually installed within a device that is comprised of a plurality of lines and containers for fluid media having different viscosity values, as well as at least one connection element, for example a cannula for coupling the device to the blood circulation of a donor. Such a device may comprise additional filters of the known type as well, for example a leukocyte depletion filter, and check valves and/or devices for producing back-up pressure, for example adjustable clamping devices in the form of roller-type clamps. It is shown, for example by the aforementioned published patent document WO 00/62840, that it is important in this connection that the mutual vertical spacing dimensions between the respective filter system and the associated containers connected upstream and downstream thereof, are maintained while the device is being in use, in order to adapt the pressure differences required for optimally operating the respective device between the source of the blood and the special filter system in the best possible manner, on the one hand, as well as between the filter system and the containers for plasma and cellular components on the other, and to maintain such spacing dimensions while the device is in operation as well.

Therefore, the present invention is based on the problem of providing a filter system by which adequately satisfactory yields of the individual components of donor blood can be obtained in practical applications as well, in order to be able in this way to cover the demand for banked blood both in the form of own and foreign blood without requiring much expenditure, whereby the filter arrangement can be integrated in a device that is adapted to an optimal separation process.

Said problem is solved by the present invention with the help of the totality of the features specified in patent claim 1 and the totality of the features specified in patent claim 12.

First of all, it has been found in this connection that it is particularly advantageous if the membrane with fine pores is realized with a U-shaped bundle of n=650 hollow fibers of the Micro PES-TF 120 type manufactured by the Akzo Faser AG. The ends of the fibers are fixed in a common perforated plate in an air-tight and germ-tight manner, and the free length of the fibers amounts to l=27 cm between the inlet and the outlet areas, whereby the perforated plate itself is fitted in the an air-tight and germ-tight manner in the open end area of a housing open only on one side, in a manner such that the free length of all hollow fibers is arranged within the housing that is closed by the perforated plate, and the inner volumes of all hollow fibers form the inlet chamber, and the outer volume of all hollow fibers between the perforated plate and the closed end of the housing forms the outlet chamber, because based on comprehensive series of tests, a hematocrit value amounting to at least 62% is always achieved with such an arrangement even in a single-stage process. With a two-stage method, which can be realized, for example with reversal of the direction of flow of the separated cellular component by the filter system into an additional collection container that can be connected to its inlet area, not only the hematocrit value specified above is always achieved, but always even a hematocrit value amounting to at least 80%, and even a hematocrit value of 90% is no rarity. Such values are distinctly above all those values obtained until now in one-stage or also two-stage filtration operations.

Advantageous further developments of the filter systems here under discussion are represented by the objects of the dependent claims 2 to 11. The dependent claims 2 to 10 relate to particularly advantageous constructional measures that substantially facilitate the manufacture of the filter systems as defined by the invention in the form of an air-tight and germ-tight, closed system that necessarily has to be sterilized as a whole before it is used, and which, therefore, can be produced at favorable cost.

The dependent claim 11 relates to the advantageous arrangement of a connection device for introducing common salt solution into the filter system as defined by the invention, such a solution serving the purpose of flushing the hydrophilic hollow fibers with said solution before their actual separation task is taking place, and to thereby assure the separation effect of the hollow fibers from the onset.

In connection with a device for the application the aforementioned filter system on the donor, it has been found to be very advantageous, furthermore, if a collection container for receiving the donor blood is connected upstream of the inlet area of the filter system, and the collection container for receiving the cellular components of the donor blood is connected downstream of the outlet area, and a collection container for receiving blood plasma is connected downstream of the outlet chamber of the filter system as well, whereby the connections between the filter system and the aforementioned containers are realized via the feed line and outlet lines in an air- and germ-tight manner, but with means of the known type without any admission of air and causing any interference effects due to undesirable pressure compensation effects, in a way such that with a preset spacing of its lower edge from the upper edge of the filter system, the collection container for receiving the blood plasma is arranged with a preset vertical spacing of its upper edge below the lower edge of the filter system, and the collection container for receiving the donor blood is arranged with its upper edge on the level of the lower edge of the filter system; and that the collection container is connected with an inlet line connected to it in an air-tight and germ-tight manner, whereby said inlet line is provided at its end facing away from the collection container with a connector element for connecting it with the blood circulation of the donor, because what is achieved with such a device is that the donor blood to be separated, after it has been collected in the predetermined site, can in fact be separated into its components or groups of components in the order of magnitude already specified above owing to the fixation of preset vertical spacing dimensions between the collection container and the filter system, on the one hand, and the filter system and the collection containers for receiving the cellular components and the blood plasma on the other hand, under pressure conditions that can be preset in an optimal manner. Said effect is advantageously increased even more if, furthermore, a leukocyte depletion filter of the known type is arranged in the feed line between the collection container and the filter system, because the filter system connected downstream is subjected to less stressed in this way, and permits more rapid separation between the blood plasma and the remaining cellular components of the blood, apart from the fact that the usually desired, largely pure erythrocyte concentrate is obtained in this way in the collection container for receiving the cellular components.

An advantageous further development of the present device is obtained as well if a drip chamber is arranged in the feed line between the collection container and the filter system, because it is possible in this way with the help of this measure to adjust and control the offer of donor blood to be separated for the filter system in a simple manner, whereby it is advantageously deemed recommendable, if a leukocyte depletion filter is installed at the same time, to arrange the drip chamber between the connection container and the leukocyte depletion filter so as the able to adjust and control the offer of donor blood to be separated in the filter system in a simple manner, as mentioned before, including the leukocyte depletion filter, on the one hand, and to assure, on the other hand, an uninterrupted, uniform flow through both the leukocyte depletion filter and the filter system and in that way also constant, preset pressure conditions in the two filter systems, which is one of the preconditions to be met for obtaining the surprising effect of a completely cell-free blood plasma as the result of using the device here under discussion.

In another embodiment of the device here under discussion, it was found to be advantageous, furthermore, if the preset vertical spacing dimension between the lower edge of the collection container and the upper edge of the filter system amounts to $a1=(100\pm20)$ cm, and/or the preset vertical spacing dimension between the lower edge of the filter system and the upper edge of the collection container for receiving the blood plasma comes to $a2=50$ cm, because optimal values of the separation of the components have been obtained with said spacing values in relevant tests.

Embodiments of the device as defined by the invention, where the outlet line of the inlet chamber is provided with a device for producing a back pressure in the filter system, have to be viewed as being advantageous as well, in particular if the device for producing a back pressure is an adjustable clamping device, or even if the clamping device is realized in the form of the roller-type clamp of the known type, because it is possible in a simple manner in that way to after-control with such a device basically all pressure conditions to be preset by means of the vertical spacing dimensions between the collection container and the filter system, on the one hand, as well as between the filter system and the connection container for receiving the cellular components and the blood plasma, on the other hand, with unavoidable variations of the adjustment parameters, for example through changes in the viscosity of the blood from one donor to the next, or the temperature variations occurring from one separation process to the next.

Advantageous further developments of the device here under discussions are obtained as well if the collection container contains, at least at the time it starts to receive blood, a preset amount of stabilizing fluid of the known type, and/or if the collection container for receiving the cellular components is pre-filled with a preset amount of a solution of additives of the known type, so that it is possible to assure in the known manner that the components of the blood or groups of components obtained therefrom can be banked over a sufficient length of time.

An embodiment of the present device, in which the connection element is a cannula, needs to be viewed as being advantageous as well, because such a cannula is a well-tested element that can be easily handled for coupling a device of the type here under discussion to the blood circulation of a donor.

An advantageous further development of the present device is obtained as well if the outlet chamber connected via the connector device for connecting a common salt solution, is coupled with a supply container for such a common salt solution in an air-tight and germ-tight manner, because this constitutes a simple method for forcibly flushing the hollow fibers to an adequate extent with physiological common salt solution before they are used, for the purpose of optimizing their efficiency for separating the components, to begin with.

Furthermore, it has to be viewed as being advantageous if the outlet line of the inlet chamber is connected in the present device in an air-tight and germ-tight manner with the feed line in the area located between the drip chamber, on the one hand, and the leukocyte depletion filter on the other, because this assures in a simple way that the blood or its components will flow through the associated lines from the collection container to the filter system without forming deposits, and from the latter to the collection containers for receiving the cellular components and the blood plasma, respectively.

Furthermore, it has been found that an embodiment of the device here under discussion is very advantageous in which the preset vertical spacing dimensions can be fixed by means of a reusable mechanical holding device comprising holding elements arranged for holding the containers and the filter arrangements in a defined manner, such a holding device being unchangeable at least while the blood is being collected, because it is assured in this way that the mutual arrangement of the individual elements of a device of the present type, which is required for each individual application of such a device, can be realized without problems in a reproducible manner especially if the individual holding elements installed, for example in the form of rigid hooks, are marked in an adequately clear way. The holding device can then be realized, for example in the form of a frame or tree mounted in a stationary manner, or in the form of a portable and rigid construction, in such a way that it can be folded together, provided such a device satisfies only the one condition that it is unchangeable within itself as the blood is being collected.

Exemplified embodiments of the filter system as defined by the invention, and of the device associated therewith are shown in the drawing, in which.

Figure 1:
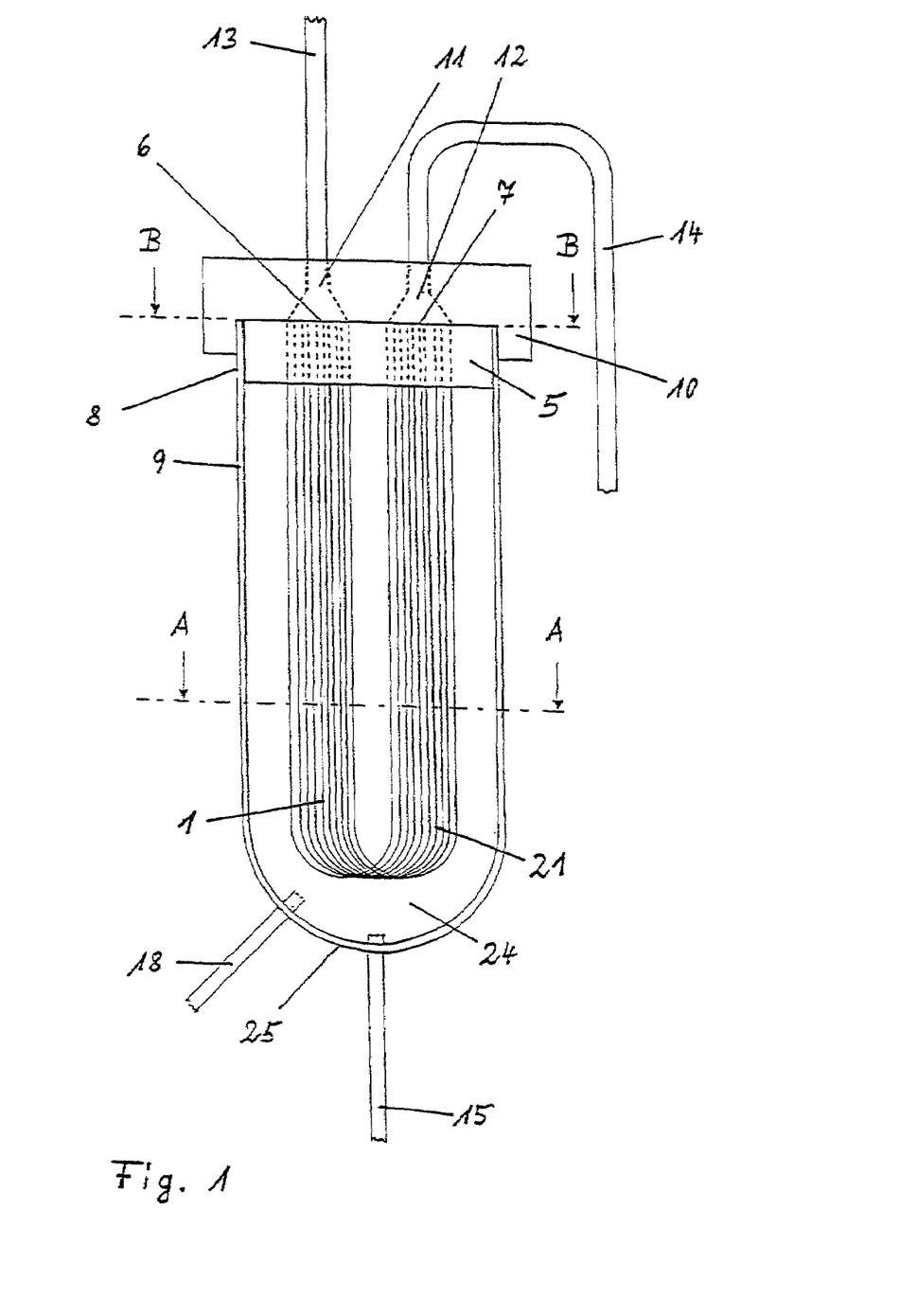
FIG. 1 shows a vertical section through a filter system as defined by the invention by a schematic and partly broken representation, as well as on a randomly selected scale.

FIG. 1 shows a vertical section through a filter system as defined by the invention by a schematic and partly broken representation, which is based on a scale selected at random. Said system comprises a U-shaped bundle l consisting of the n=650 hollow fibers 21 of the Mircro PES-TF 10-type of the Akzo Faser AG corporation. Each fiber has a free length l=27 cm. The ends of said fibers are fixed in an air-tight and germ-tight manner in a common perforated plate 5, where such ends form an inlet area 6 and an outlet area 7. Said areas are clearly visible in FIG. 3. The free length of l=27 cm is understood to be the length of each hollow fiber 21 extending from the underside of the perforated plate 5 up to the point where the fiber reaches again the underside of the perforated plate 5. The total length of each hollow fiber 21 results from twice the addition of the thickness of the perforated plate 5 to the free length of l=27 cm. The perforated plate may be made of any desired material such as, for example quartz, and may have a preset thickness of, for example 3 cm. In the case shown, said plate is fitted in an air- and germ-tight manner into the upper end zone 8 of a housing 9. Said housing is open only at one of its ends, preferably at the upper end. A closing cap 10 is arranged on the perforated plate 5 an the upper edge zone 8. Said cap has the two passages 11, 12, for connecting the inlet area 6, on the one hand, and the outlet area 7, on the other hand, with the outer volume of the housing 9. The closing cap 10 is connected with the perforated plate 5 and the upper edge zone 8 in an air- and germ-tight manner as well, preferably by means of gluing.

Figure 2:
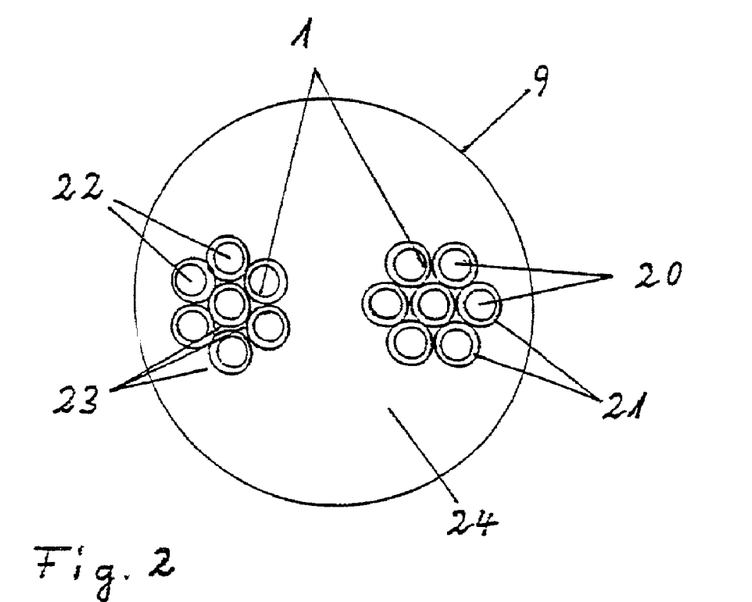
FIG. 2 shows the section along line A—A in FIG. 1 by an enlarged and simplified schematic representation.

An inlet line 13 for feeding donor blood extends from the passage 11, and an outlet line 14 of the inlet chamber 22 extends from the passage 12 (see FIG. 2). The two lines 13 and 14 are fixed in the passages 11 and, respectively, 12 in an air- and germ-tight manner. In another site of the housing 9, preferably but not necessarily located at its end disposed opposite the perforated plate 5, an outlet line 15 of the outlet chamber 24 connected with said end in an air- and germ-tight way is extending from said end. Said outlet chamber is formed in the housing 9 below the perforated plate 5 by the external volume 23 (see FIG. 2) of the totality of the hollow fibers 21, exactly in the same way in which the inlet chamber 22 is formed by the totality of the inner volumes 20 (see FIG. 2) of the hollow fibers 21 between the inlet area 6 and the outlet area 7 of the perforated plate 5 (see FIG. 3).

The blood and its components are preferably transported there by force of gravity even though various developments have existed where provision was made for effecting such a transport by means of an internal or external generation of a vacuum, which, however, it not to be excluded in the present case.

FIG. 1, furthermore, shows a connector device 18 of the known type for admitting a solution of common salt for flushing the hydrophilic hollow fibers 21 prior to their absorption of donor blood. Said connector device is arranged on the housing 9 in the region of the outlet chamber 24.

FIG. 2 shows the section A—A from FIG. 1, which, by an enlarged and simplified schematic representation, discloses the structure of the bundle 1 of the n=650 hollow fibers 21 of the type specified above. Only a few of these fibers are shown here for illustration purposes. A multitude of the hollow fibers 21 are forming with the totality of their inner volumes 20 the inlet chamber 22, which, by way of the feed line 13 that has already been mentioned above a number of times, is connected with the donor, on the one hand, and, on the other hand, with the collection container for receiving the cellular components of the blood via the outlet line 14, which has already been mentioned above a number of times as well. The external volume 23 of all of the hollow fibers 21, on the other hand, is forming within the housing 9 the outlet chamber 24, which is connected with a collection container for receiving the plasma via the outlet line 15, which already has been mentioned above a number of times as well.

Figure 3:
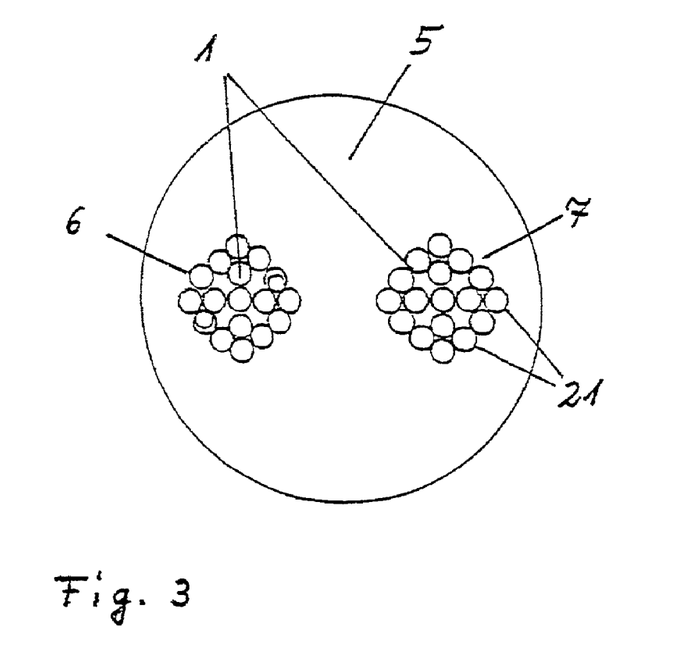
FIG. 3 shows the section along lien B—B in FIG. 1 by an enlarged and simplified schematic representation.

FIG. 3 shows the section B—B from FIG. 1, which, by an also enlarged and simplified schematic representation, shows the top view of the perforated plate 5 with the closing cap 10 removed, and thus illustrates the inlet area 6 and the outlet area 7.

Figure 4:
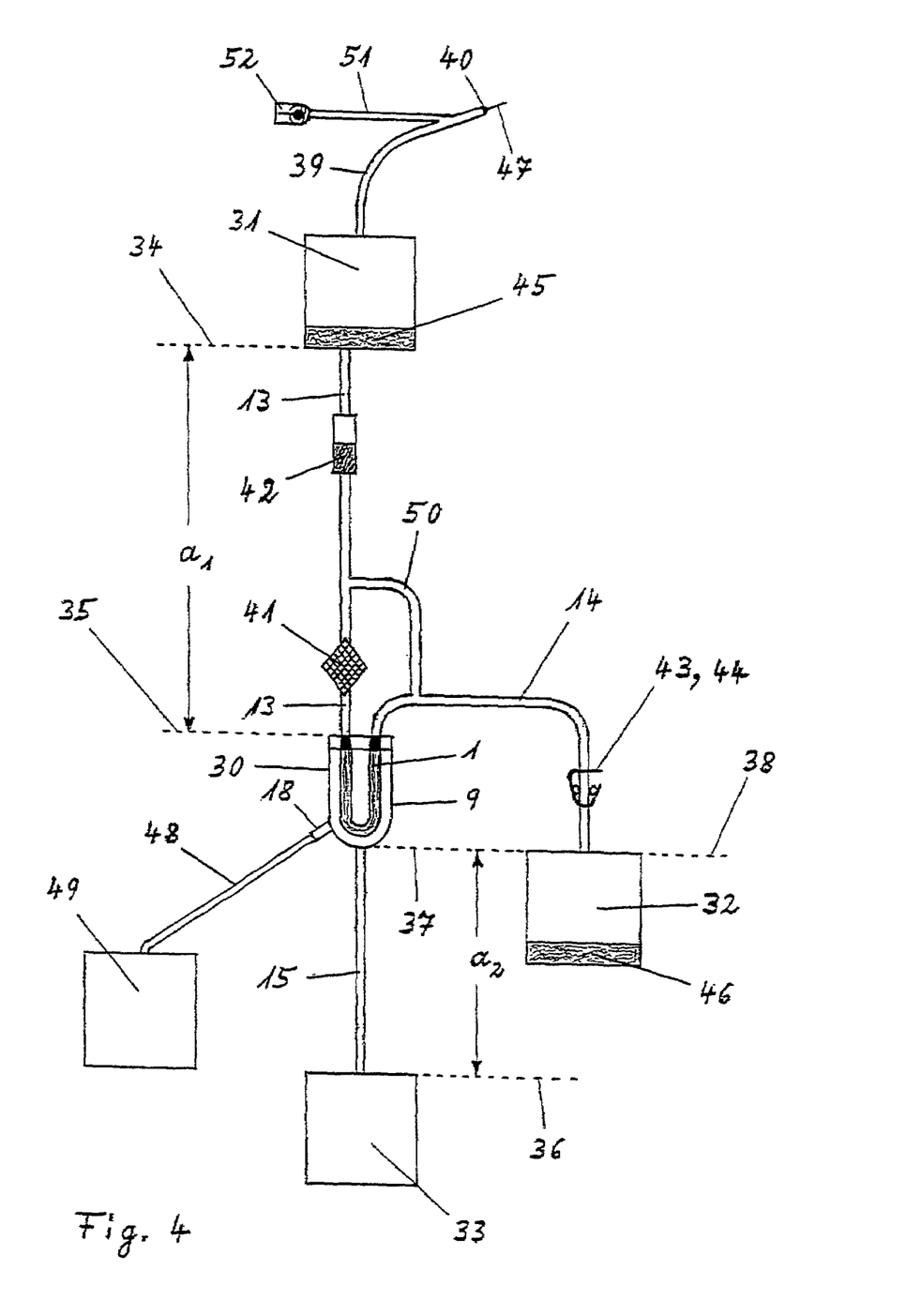
FIG. 4 shows by a schematic representation a view of a device for application of the filter system according to FIGS. 1 to 3 on the donor.

FIG. 4 shows by a schematic representation the view of a device for application of the filter system according to FIGS. 1 to 3 on the donor. In the present case, said device, to begin with, is comprised of a collection container 31 consisting in the present case—but not necessarily so—of a pouch-like hollow body made of plastic sheet material, which is assumed to be known. Said container is connected in an air- and germ-tight manner with an inlet line 3, on the one hand, and an inlet line 13 leading to a filter system 30 on the other. It is assumed in connection with said lines, as it has been also in connection with all other connection lines described in the following as well, without limiting the generality, that such connecting lines are hose-type connection elements of the known type made of elastic plastic material. At its end facing away from the collection container 31, the inlet line 39 supports a connector element 40 that can be coupled to one or more blood vessels of a donor. It is assumed in the present case that said connection element is a cannula 47 of the conventional type, but must not necessarily be such a cannula. It is, of course, possible to replace such a cannula with any other suitable element working in the same mode of operation.

The feed line 13 is first leading to a drip chamber 42 installed in said line in an air- and germ-tight way. Said drip chamber preferably serves the purpose of switching on and controlling the amount of donor blood supplied to the filter system 30 per unit of time. Via the continuation of the feed line 13, the drip chamber is connected with a leukocyte depletion filter 41 of the known type, which is installed in the feed line 13 in an air- and germ-tight manner as well.

It is not mandatory to arrange the leukocyte depletion filter in the site specified above; however, this has the advantage that the filter system 30 connected downstream, which already has been described in detail above, will be stressed to a lesser degree in this way and therefore permits separating the blood plasma and the remaining components of the blood at a higher rate, whereby, furthermore, it is possible to achieve the frequently desired separation of the leukocytes and, at the same time of the thrombocytes from the other components of a charge of donor blood to be separated. Moreover, the shown installation of the leukocyte depletion filter 41 directly upstream of the filter system 30 assures an uninterruptedly uniform flow of the donor blood to be separated through the two aforementioned filter systems 30 and 41 and thus constant preset pressure conditions in said systems as well, which is one of the preconditions to be satisfied for the surprising effect that the device here under discussion will produce a completely cell-free blood plasma in the collection container 33 for receiving the blood plasma. This is explained in greater detail farther below.

As described before, the filter system 30 is comprised of a bundle 1 of the hollow fibers 21, which can be impregnated with physiological common salt solution, whereby the totality of the inner volumes 20 of the hollow fibers 21 is forming an inlet chamber 22, and the outer volume of all of the hollow fibers 21 is forming an outlet chamber 24. Via an outlet line 15 connected to it, the outlet chamber 24 is then connected in an air- and germ-tight manner with a collection container 33 for receiving the blood plasma. Said collection container is connected with the outlet line 15 in an air- and germ-tight manner as well. The inlet chamber 22 itself is connected via an outline line 14 with a collection container 32 for receiving the cellular components. Also there, all points of connection are, of course, realized in an air- and germ-tight manner. In connection with the device here under discussion, the collection container 32 for receiving the cellular components substantially immediately receives a largely pure erythrocyte concentrate. Concerning the reference numerals specified above, reference is partly made to FIGS. 1 and 2 because using all of the reference numerals defined there in the present FIG. 4, would considerably impair the clarity of the latter figure.

For the filter system 30 to function in an optimal way, a special adjustment of the pressure conditions is required within the overall system of the present device; however, it is in particular necessary to make provision that a back pressure—that has to be preset—can be produced in the filter system 30. Such a back pressure can be generated by maintaining preset vertical spacing dimensions between the individual components of the device, especially between the collection container 31 and the filter system 30, on the one hand, and between the collection containers 32 and 33 for receiving the cellular components of the donor blood on the other. This can be accomplished, for example by suspending the individual elements of the device during each collection of blood on specially characterized holding elements, for example on rigid hooks of a mechanical holding device that cannot be altered at least in the course of each collection of blood. The latter can be advantageously reused and, furthermore, can be arranged, for example in a stationary or mobile manner in the form of a frame or tree, and it may be a rigid or foldable device as long as it will be unchangeable within itself during each collection of blood, and will permit arranging the devices here under discussion in a reproducible way. In the exemplified embodiment shown, for example, an optimal hematocrit value is obtained if the spacing dimension between the lower edge 34 of the collection container 31 and the upper edge 35 of the filter system 30 amounts to $a1=(100\pm20)$ cm, and the spacing dimension between the lower edge 37 of the filter system 30 and the upper edge 36 of the collection container 33 for receiving blood plasma comes to $a2=50$ cm, while the upper edge 38 of the collection container 32 for receiving the cellular components of the donor blood is disposed at the level of the lower edge 37 of the filter system 30.

The spacing dimension $a1$ can be realized for achieving an optimal separation of the donor blood, for example by an arrangement in which a spacing of $a11=30$ cm is selected between the collection container 31 and the drip chamber 32; a spacing of $a12=13$ cm is selected between the drip chamber 42 and a breaking valve of the known type that is not explicitly shown here, for starting the flow of blood from the collection container 31 to the filter system 30 in a targeted manner; and, furthermore, a spacing dimension of $a13=23$ cm is selected between the breaking valve and the inlet of a venting line 50 located in the feed line 13, said venting line being explained in detail farther below; a spacing dimension $a14=12$ cm is selected between the inlet of the venting line 50 and the leukocyte depletion filter 41; and a spacing dimension of $a15=12$ cm is selected between the leukocyte depletion filter 41 and the filter system 30, whereby the total length of the drip chamber 42, the breaking valve and the leukocyte depletion filter 41 has to be added to the sum of the above spacing dimensions $a11$ to $a15$. In this connection, a length of $lE=30$ cm can be assigned to the venting line 50, whereby its outlet is arranged with a spacing dimension of $a=5$ cm from the outlet of the drain line 14 from the filter system 30. This arrangement, of course, can be replaced by any other arrangement that will produce identical pressure conditions in the filter system 30, with otherwise unchanged parameters.

In addition to the arrangement of the elements described above that are arranged in a preset manner in terms of space, the device shown, furthermore, yet comprises still another device 43 for producing a back pressure in the filter system 30. Such an additional device can be realized, for example in the form of an adjustable clamping device mounted on the outlet line 14 of the inlet chamber 22, in the present case in the form of a roller clamp 44 of the known type. Such a roller clamp preferably, but not exclusively serves the purpose of permitting in a simple manner correction and after-adjustment measures in the event unavoidable variations occur in the adjustment parameters for setting the pressure conditions in the overall system of the device, for example if changes occur in the viscosity of the blood from one donor to another, or if temperature fluctuations occur from one separation process to another. Furthermore, a venting line 50 connected with the drain line 14 in an air- and germ-tight manner is branching off the latter, said venting line in turn being connected in an air- and germ-tight manner with the feed line 13 in the area between the drip chamber 42 and the leukocyte depletion filter 41. Said venting line prevents the blood or its components from forming any disturbing deposits in the lines 13, 14 and 15, and in the filter systems 30 and 41.

Before the entire device is sterilized, the collection container 31 is usually already filled with a stabilizing fluid 45, for example CPD, and the collection container 32 for receiving the cellular components of the donor blood is provided in the same way with an additive solution 46, for example SAG Manitol. Both measures serve the purpose of securing an adequate duration of preservation for the blood components produced.

Furthermore, for the required flushing of the hydrophilic hollow fibers 21 with a physiological solution of common salt before the separation process is carried out, the filter system 30 is connected in an air-and germ-tight manner with a supply reservoir 49 for such a common salt solution via a connecting device 18 and a flushing line 48.

For drawing donor blood for control tests, the present device, furthermore, comprises a test line 51 that is branching off in an air- and germ-tight manner from the inlet line 39 in the area between the connecting element 40 and the collection container 31 located preferably, but not necessarily within the proximity of the connecting element 40. The end of said test line that is facing away from the inlet line 39, is feeding into a drawing valve 52 of the known type that has to be opened by generating external pressure.

All air- and germ-tight connections are either glued or welded seams or coupling elements of the known type, which are not explicitly shown and described herein because the expert in the field is familiar with them. The same applies to throw-away clamps or breaking valves that may have to be mounted in the lines 13, 14, 15 and 50, so that a line, for example the feed line 13 can be opened in the specified site only when needed, for example in the site located between the drip chamber 42 and the inlet of the venting line 50, or in order to prevent in a case of emergency or during any dismantling of the device any unintended air deflation or sudden pressure changes from occurring in the containers 32 and 33 filled with the separated components of the blood, or also in the supply reservoir 49, after the separation processes have been completed.

The present patent claim, of course, relates not only to the exemplified embodiments explicitly described above in detail, but also to all conceivable embodiments of the inventive idea constituting the basis for the present patent application that are covered by the scope of protection of the following patent claims 1 and 12.

| List of Reference Numerals | | |
|---|---|---|
| 1 | | Bundle of hollow fibers |
| 5 | | Perforated plate |
| 6 | | Inlet area |
| 7 | | Outlet area |
| 8 | | Open end area |
| 9 | | Housing |
| 10 | | Closing cap |
| 11, 12 | | Passages |
| 13 | | Feed line for donor blood |
| 14 | | Outlet line of inlet chamber |
| 15 | | Outlet line of outlet chamber |
| 18 | | Connecting device for common salt solution |
| 20 | | Inner volumes |
| 21 | | Hollow fibers |
| 22 | | Inlet chamber |
| 23 | | Outer volume |
| 24 | | Outlet chamber |
| 25 | | Closed end |
| 30 | | Filter system |
| 31 | | Collection container |
| 32 | | Collection container for receiving the cellular components of the donor blood |
| 33 | | Collection container for receiving blood plasma |
| 34 | | Lower edge of collection container |
| 35 | | Upper edge of filter system |
| 36 | | Upper edge of collection container for blood plasma |
| 37 | | Lower edge of filter system |
| 38 | | Upper edge of collection container for receiving cellular components of the donor blood |
| 39 | | Inlet line |
| 40 | | Connector element |
| 41 | | Leukocyte depletion filter |
| 42 | | Drip chamber |
| 43 | | Device for producing back pressure |

-continued

| List of Reference Numerals | | |
|---|---|---|
| 44 | | Roller-type clamp |
| 45 | | Stabilizing fluid |
| 46 | | Additive solution |
| 47 | | Cannula |
| 48 | | Rinsing line |
| 49 | | Supply reservoir for common salt solution |
| 50 | | Venting line |
| 51 | | Test line |
| 52 | | Drawing valve |

The invention claimed is:

1. A gravity driven device for filtering a donor's blood comprising:
   a) a filter arrangement for the separation of blood into plasma and cellular components, comprising:
   a housing having an open end area and a closed end area;
   an inlet line coupled to said housing for feeding donor blood into said open end area of said housing;
   an outlet line coupled to said housing for letting blood flow out of said open end area of said housing;
   a perforated plate having perforations disposed in said housing for coupling to both said inlet line and said outlet line; and
   a U-shaped fine membrane disposed below said perforated plate and formed from hollow fibers wherein said U-shaped fine membrane is fixed in an air-tight manner to said perforated plate wherein said perforations in said perforated plate form an opening for said hollow fibers, and wherein said hollow fibers form an inlet chamber and a remaining region of said housing outside of said hollow fibers forms an outlet chamber;
   b) a collection container for receiving the donor's blood upstream of said inlet line of said housing wherein said donor blood collection container has a vertical lower edge that is positioned with a preset vertical spacing above an upper edge of the filter arrangement;
   c) a feed line for fluid communication between said donor blood collection container and said filter arrangement;
   d) a collection container for receiving cellular components of the donor's blood downstream from said outlet area of the filter system such that a vertical upper edge of said cellular components collection container is disposed approximately at the vertical level of the lower edge of the filter arrangement;
   e) a collection container for receiving blood plasma downstream from said outlet chamber of the filter arrangement wherein said blood plasma collection container has an upper edge that is disposed at a vertical level lower than the lower edge of the filter arrangement wherein a set of connections between said filter arrangement, said collection containers via said inlet line, said outlet line to said inlet chamber, and said outlet line for said outlet chamber are germ tight, but can be broken via any known means without admitting air or causing interfering effects;
   f) a connector element in fluid communication with said donor blood collection container wherein said connector element is coupled to the donor to draw blood from the dohor into said donor blood connection container;
   g) a leukocyte depletion filter coupled to said feed line between said blood donor collection container and the filter arrangement; and h) a venting, connecting said outlet line to said feed line, upstream of said leukocyte depletion if filter.

2. The filter arrangement as in claim 1, further comprising a closing cap coupled to said open end area of said housing, wherein said closing cap has a release passage leading to an inlet area and outlet area of said perforated plate, wherein said closing cap is connected in an air and germ tight manner with a surface of said perforated plate and also coupled to an open end of said housing.

3. The filter arrangement as in claim 2, wherein said perforated plate and said closing cap have an air and germ tight connection, and wherein said passages to said inlet area and said outlet area and to said feed line for donor blood and for said outlet line of said inlet chamber for said cellular components are air and germ tight connections.

4. The filter arrangement as in claim 1, wherein said perforated plate has a thickness of 3 cm and wherein a total length of each of said hollow fibers is 33 cm.

5. The filter arrangement as in claim 1, further comprising an second outlet line coupled to said outlet chamber, wherein said second outlet line is arranged at a closed end of said housing.

6. The filter arrangement as in claim 1, wherein said housing is made from glass.

7. The filter arrangement as in claim 1, wherein said housing is made from plastic.

8. The filter arrangement as in claim 7, wherein said housing is made from polyurethane.

9. The filter arrangement as in claim 5, further comprising a connector device coupled to said outlet chamber, said connector device for introducing a common salt solution for flushing said fibers before blood is received.

10. The device as in claim 1, further comprising a drip chamber disposed in said feed line between said blood donor collection container and said filter arrangement.

11. The device as in claim 1, further comprising a drip chamber disposed between said blood donor collection container and said leukocyte depletion filter.

12. The device as in claim 1, wherein said preset vertical spacing between said lower edge of said blood donor collection container and the upper edge of said filter arrangement is between 80 and 120 cm.

13. The device as in claim 1, wherein said preset vertical spacing between said lower edge of said filter arrangement and said upper edge of said cellular component collection container is approximately 50 cm.

14. The device as in claim 1, further comprising a device for producing back pressure in said filter arrangement coupled to said outlet line of said inlet chamber.

15. The device as in claim 14, wherein said device for producing back pressure is an adjustable clamping device.

16. The device as in claim 15, wherein said adjustable clamping device is in the form of a roller type clamp.

17. The device as in claim 1, wherein said blood donor collection container contains a preset amount of stabilizing fluid during the time of drawing blood.

18. The device as in claim 1, wherein said cellular component collection container further includes a preset amount of additive solution.

19. The device as in claim 1, wherein said connecting element is a cannula.

20. The device as in claim 1, further comprising a supply reservoir in fluid communication with said outlet chamber of said filter arrangement via a connector device.

21. The device as in claim 10, further comprising a venting line, wherein said outlet line of said inlet chamber is connected in an air and germ tight manner by means of said venting line, and wherein said venting line is coupled to said feed line between said drip chamber and said leukocyte depletion filter.

22. The device as in claim 1, further comprising at least one reusable mechanical holding device wherein the preset vertical spacing dimensions between said collection containers, and said filter arrangement can be fixed by said reusable mechanical holding device in a defined manner, wherein said reusable mechanical holding device is unchangable during a time the donor's blood is drawn.

23. The gravity driven blood filtering device according to claim 1 wherein said U-shaped membrane is formed from a bundle of n=650 hollow fibers.

* * * * *